United States Patent
Stivanello et al.

(10) Patent No.: US 10,385,020 B2
(45) Date of Patent: Aug. 20, 2019

(54) PROCESS INTERMEDIATES AND METHODS FOR THE PREPARATION OF PROCESS INTERMEDIATES FOR THE SYNTHESIS OF ARGATROBAN MONOHYDRATE

(71) Applicant: LUNDBECK PHARMACEUTICALS ITALY S.p.A., Padua (IT)

(72) Inventors: Mariano Stivanello, Schio (IT); Florian Anton Martin Huber, Dolo (IT); Antonio Ricci, Spoltore (IT)

(73) Assignee: LUNDBECK PHARMACEUTICALS ITALY S.P.A., Padua (IT)

( * ) Notice: Subject to any disclaimer, the term of this patent is extended or adjusted under 35 U.S.C. 154(b) by 0 days.

(21) Appl. No.: 15/976,927

(22) Filed: May 11, 2018

(65) Prior Publication Data

US 2018/0258041 A1   Sep. 13, 2018

Related U.S. Application Data

(60) Continuation of application No. 15/235,488, filed on Aug. 12, 2016, now Pat. No. 9,994,526, which is a division of application No. 14/009,529, filed as application No. PCT/EP2012/055331 on Mar. 26, 2012, now abandoned.

(30) Foreign Application Priority Data

Apr. 4, 2011 (IT) .............................. MI2011A0545

(51) Int. Cl.
    *C07D 211/60* (2006.01)
    *C07D 401/12* (2006.01)

(52) U.S. Cl.
    CPC .......... *C07D 211/60* (2013.01); *C07D 401/12* (2013.01)

(58) Field of Classification Search
    USPC ....................................................... 546/245
    See application file for complete search history.

(56) References Cited

U.S. PATENT DOCUMENTS

| | | | |
|---|---|---|---|
| 4,201,863 A | 5/1980 | Okamoto et al. | |
| 4,234,577 A | 11/1980 | Franz Fiedler | |
| 6,440,417 B1 | 8/2002 | Thibaudeau et al. | |
| 7,087,769 B1 | 8/2006 | Contijoch Mestres et al. | |

FOREIGN PATENT DOCUMENTS

| | | |
|---|---|---|
| CN | 101235031 A | 8/2008 |
| CN | 100427480 C | 10/2008 |
| EP | 0008746 A1 | 3/1980 |
| EP | 0823430 A1 | 2/1998 |
| JP | S5533499 A | 3/1980 |
| JP | S5615267 A | 2/1981 |
| JP | S5692213 A | 7/1981 |
| JP | S56104866 A | 8/1981 |
| JP | H02212473 A | 8/1990 |
| JP | 2003160560 A | 6/2003 |
| WO | 2009124906 A2 | 10/2009 |

OTHER PUBLICATIONS

Joel Bernstein, Polymorphism in Molecular Crystals, IUCr Monographs on Crystallography, 2002, p. 4-5, International Union of Crystallography.
Kikumoto et al., Arylsulfoniyl, 1980, CA93:150667.
Kenneth R. Seddon, Pseudopolymorph: A Polemic, Crystal Growth & Design, Oct. 19, 2004. V. 4 No. 6, p. 1087, American Chemical Society.
Solvate, The Free Dictionary, from internet (2014), p. 1.
Berger, Finding An Empirical Formula And Molecular Formula, Nov. 10, 2016, https://chemberger.wordpress.com.
Stoichiometry, 2009, p. 1-5, David N. Blauch, https://www.davidson.edu.
Japan Org. Chemistry, 1958, p. 1-5.
Kikumoto et al., a-(N-Arylsulfonyl-L-argininamides and pharmaceutical compositions containing these substances, 1980, CA93:150657.
Mitsubishi, (2R,4R)-4-Methyl-2-piperidinecarboxylic acid and its L-tartrate salt,1982, CA96:35103.
Etemad-Moghadam et al., Syntheses of Nα-(β-naphthylsulfonylglycyl)argininamides as potential selective synthetic thrombin inhibitors, 1980, CA111:233573.
Sudha R. Vippagunta, Harry G. Brittain, David J.W. Grant, Crystalline Solids, Advanced Drug Delivery Reviews 48 (2001), 3-26, Elsevier Science B.V.
Barbara Rodriguez-Spong, Christopher P. Price, Adivaraha Jayasankar, Adam J. Matzger, Nair Rodriguez-Hornedo, General principles of pharmaceutical solid polymorphism: a supramolecular perspective, Advanced Drug Delivery Reviews 56 (2004), 241-274, Elsevier Science B.V.
J. Keith Guillory, Generation of Polymorphs, Hydrates, Solvates, and Amorphous Solids, Polymorphism in Pharmaceutical Solids, 1999, 1, 2, 183-266, Harry G. Brittain Discovery Laboratories Inc. New Jersey, Marcel Dekker Inc., New York.

*Primary Examiner* — Patricia L Morris
(74) *Attorney, Agent, or Firm* — Henry J. Cittone; Cittone Demers & Arneri LLP

(57) ABSTRACT

Methods are provided for the synthesis of key intermediates for the synthesis of Argatroban monohydrate, ethyl (2R,4R)-1-[(2S)-2-amino-5-[[imino(nitroamino)methyl]amino]-1-oxopentyl]-4-methylpiperidine-2-carboxylate compounded with HCl. Such intermediates are also provided.

6 Claims, No Drawings

PROCESS INTERMEDIATES AND METHODS FOR THE PREPARATION OF PROCESS INTERMEDIATES FOR THE SYNTHESIS OF ARGATROBAN MONOHYDRATE

CROSS REFERENCE TO RELATED APPLICATIONS

This application is a continuation application of U.S. Ser. No. 15/235,488 filed Aug. 12, 2016 which is a divisional of U.S. application Ser. No. 14/009,529 filed Dec. 9, 2013 which is a National Phase application of PCT International Application No. PCT/EP2012/055331, International Filing Date, Mar. 26, 2012, claiming priority to Italian Patent Application No. MI2011A000545, filed Apr. 4, 2011, each of which is hereby incorporated by reference in its entirety. To the extent appropriate, a claim of priority is made to each of the above disclosed applications.

FIELD OF THE INVENTION

An object of the present invention is a method for the synthesis of a key intermediate for the synthesis of Argatroban monohydrate, ethyl (2R,4R)-1-[(2S)-2-amino-5-[[imino(nitroamino)methyl]amino]-1-oxopentyl]-4-methylpiperidine-2-carboxylate compounded with HCl.

BACKGROUND OF THE INVENTION

Argatroban monohydrate is a synthetic derivative of L-arginine having an anticoagulant activity in that it directly and reversibly inhibits thrombin or the formation thereof.

The preparation of Argatroban monohydrate starting from (2R,4R)-1-[$N^G$-nitro-$N^2$-(3-methyl-8-quinolinesulfonyl)-L-arginyl]-4-methyl-2-piperidine carboxylic acid is described in WO2009124906.

EP0008746 describes how to obtain Argatroban starting from (2R,4R)-1-[$N^G$-nitro-$N^2$-(3-methyl-8-quinolinesulfonyl)-L-arginyl]-4-methyl-2-piperidine carboxylic acid, wherein the peptide coupling is obtained through the formation of an anhydride mixed with isobutyl chloroformate.

Also EP0823430 describes how to obtain Argatroban starting from (2R,4R)-1-[$N^G$-nitro-$N^2$-(3-methyl-8-quinolinesulfonyl)-L-arginyl]-4-methyl-2-piperidine carboxylic acid and performs the peptide coupling in presence of phosphoryl chloride.

Obtaining 1-[$N^G$-nitro-$N^2$-(3-methyl-8-quinolinesulfonyl)-L-arginyl]-4-methyl-2-piperidine carboxylic acid starting from N-nitro-arginine was described in U.S. Pat. No. 4,201,863. U.S. Pat. No. 4,201,863 reacts protected N-nitro arginine such as Boc anhydride with isobutyl chloroformate, so as to obtain a mixed anhydride which is then reacted with 4-methyl-2-piperidine carboxylic ethyl ester acid to obtain 2-piperidine carboxylic acid, 1-[2-amino-5-[[imino(nitroamino)methyl]amino]-1-oxopentyl]-4-methyl-ethyl ester, hydrochloride as a mixture of diastereoisomers.

The resolution of the pipecolic intermediate, used in the synthesis processes described above, is indicated in JP2212473 wherein racemic ethyl 4-methylpiperidine-2-carboxylate is exposed to L-tartaric acid in aprotic polar solvent or in the same solvent mixed with an alcohol so as to form the diastereomeric salt of (2R,4R)-4-methylpiperidine-2-carboxylate with L-tartaric acid, which is subjected to precipitation and purification. The removal of L-tartaric acid leads to the desired compound. Following the resolution procedure as described in JP2212473, the purity of the isolated products is extremely variable and the process reveals poor yields.

Thus, there strongly arises the need for a synthetic process which leads to obtaining the ethyl (2R,4R)-1-[(2S)-2-amino-5-[[imino(nitroamino)methyl]amino]-1-oxopentyl]-4-methylpiperidine-2-carboxylate intermediate, which is essential in the processes described for the synthesis of Argatroban, in a rapid manner, reducing costs, with high yields and capable of preventing the resolution of the pipecolic intermediate and possibly limiting or excluding highly toxic substances, such as for example alkyl chloroformates.

SUMMARY OF THE INVENTION

The present invention describes a method for diastereoselectively obtaining ethyl (2R,4R)-1-[(2S)-2-amino-5-[[imino(nitroamino)methyl]amino]-1-oxopentyl]-4-methylpiperidine-2-carboxylate compounded with HCl, to be used as an advanced intermediate in the synthesis of Argatroban.

DETAILED DESCRIPTION

The present invention describes the high yield obtainment of ethyl (2R,4R)-1-[(2S)-2-amino-5-[[imino(nitroamino)methyl]amino]-1-oxopentyl]-4-methylpiperidine-2-carboxylate compounded with HCl (1), solvated or unsolvated, starting from a mixture of the same ethyl (2R,4R)-1-[(2S)-2-amino-5-[[imino(nitroamino)methyl]amino]-1-oxopentyl]-4-methylpiperidine-2-carboxylate (1) and the diastereoisomer thereof, ethyl (2S,4S)-1-[(2S)-2-amino-5-[[imino(nitroamino)methyl]amino]-1-oxopentyl]-4-methylpiperidine-2-carboxylate (2).

The obtainment of ethyl (2R,4R)-1-[(2S)-2-amino-5-[[imino(nitroamino)methyl]amino]-1-oxopentyl]-4-methylpiperidine-2-carboxylate compounded with HCl (1), solvated or unsolvated, is carried out through selective precipitation and ensuing isolation thereof.

The expression "compounded with HCl" is used to indicate a compound with an HCL content comprised between 1 mol/mol and 2 mol/mol; the term "dihydrochloride" is used to indicate a compound having a content (weight/weight) of chlorides comprised between 12 and 16%; the term "solvate" is used to indicate a compound having an organic solvent or water content of at least 0.5 mol/mol. The expression "exposure to the solvent" is used to indicate the treatment of compounds, whether liquid or solid, using the indicated solvent. Alternatively, the same compounds may be generated in the same solvent.

In particular, the present invention describes how to obtain ethyl (2R,4R)-1-[(2S)-2-amino-5-[[imino(nitroamino)methyl]amino]-1-oxopentyl]-4-methylpiperidine-2-carboxylate dihydrochloride (3) compounds and ethyl (2R,4R)-1-[(2S)-2-amino-5-[[imino(nitroamino)methyl]amino]-1-oxopentyl]-4-methylpiperidine-2-carboxylate dihydrochloride solvated by ethanol (4) starting from a mixture of the two ethyl (2R,4R)-1-[(2S)-2-amino-5-[[imino(nitroamino)methyl]amino]-1-oxopentyl]-4-methylpiperidine-2-carboxylate compounded with HCl (1) and ethyl (2S,4S)-1-[(2S)-2-amino-5-[[imino(nitroamino)methyl]amino]-1-oxopentyl]-4-methylpiperidine-2-carboxylate compounded with HCl (2) diastereoisomers.

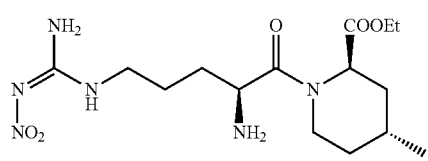

composto con HCl
(1)

+

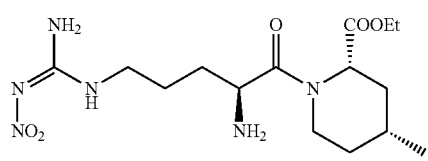

composto con HCl
(2)

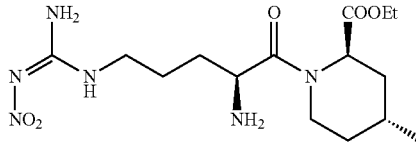

composto con HCl
(1)

composto dicloridrato: 3
composto dicloridrato solvato
(solvato=EtOH: 4)

Legenda:
Composto con HCl=compound with HCl
Composto dicloridrato solvato=dihydrochloride solvated compound
Solvato=solvated Said mixture of diastereoisomers may be obtained from analogous compounds wherein the 2-amino group may be suitably protected with a protector group used in the chemistry of the peptides.

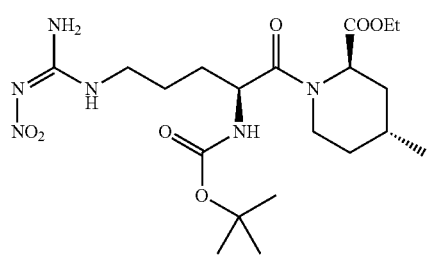

5

+

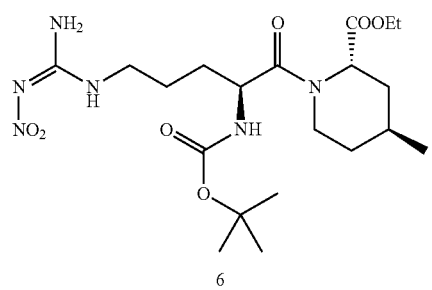

6

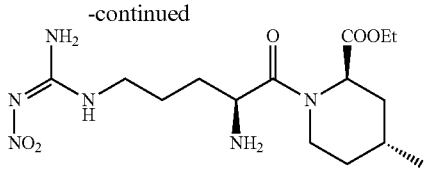

composto con HCl
(1)

+

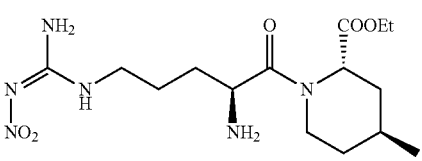

composto con HCl
(2)

Composto=compound

In a preferred embodiment, said protection is obtained by forming a tert-butyl carbamate (Boc) and the initial mixture is thus constituted by ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and by ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6).

The two diastereoisomers 5 and 6 are obtained by peptide coupling the racemic base or hydrochloride (7, 8) ethyl trans-(±)-4-methylpiperidine-2-carboxylate ester or, alternatively, the mixture of ethyl (2R,4R)-4-methylpiperidine-2-carboxylate (9) and ethyl (2S,4S)-4-methylpiperidine-2-carboxylate (10), enriched with ethyl (2R,4R)-4-methylpiperidine-2-carboxylate (9) with N-Boc-N'-nitro-L-arginine.

The peptide coupling is carried out with a quite high yield and chemical purity.

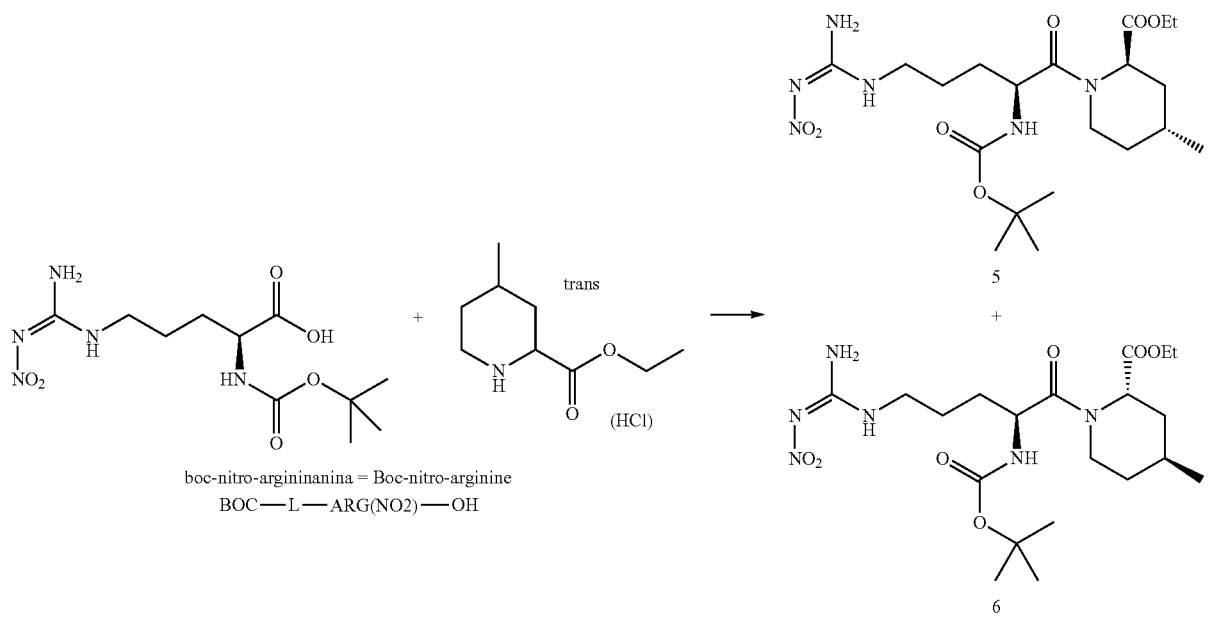

boc-nitro-argininanina = Boc-nitro-arginine
BOC—L—ARG(NO2)—OH

Boc-nitro-arginina=Boc-nitro-arginine

Furthermore, the synthesis of said racemic ester as a free base (7) or as a hydrochloride (8) is described.

Purifying ethyl (2R,4R)-1-[(2S)-2-amino-5-[[imino(nitroamino)methyl]amino]-1-oxopentyl]-4-methylpiperidine-2-carboxylate compounded with HCl, solvated or unsolvated forms a further object of the present invention.

The drying process through which, starting from the wet product, the solvated or unsolvated form thereof is obtained forms a further object of the present invention.

Deprotection and Isolation of ethyl (2R,4R)-1-[(2S)-2-amino-5-[[imino(nitroamino)methyl]amino]-1-oxopentyl]-4-methylpiperidine-2-carboxylate Compounded with HCl (1), Solvated or Unsolvated The isolation of the aforementioned compound (1) is performed according to a process comprising:

a) exposing a mixture of ethyl (2R,4R)-1-[(2S)-2-amino-5-[[imino(nitroamino)methyl]amino]-1-oxopentyl]-4-methylpiperidine-2-carboxylate compounded with HCl, solvated or unsolvated, and ethyl (2S,4S)-1-[(2S)-2-amino-5-[[imino(nitroamino)methyl]amino]-1-oxopentyl]-4-methylpiperidine-2-carboxylate compounded with HCl, solvated or unsolvated, to an organic solvent, preferably selected from among an alcohol, an ester or a mixture thereof at a temperature comprised between 0° C. and the reflux temperature, preferably between 20 and 55° C.;

b) selective precipitation of ethyl (2R,4R)-1-[(2S)-2-amino-5-[[imino(nitroamino)methyl]amino]-1-oxopentyl]-4-methylpiperidine-2-carboxylate compounded with HCl, solvated or unsolvated;

c) optionally, diluting the suspension obtained in step b) with an ester or alcohol or with an ester/alcohol mixture and, optionally, heating before or after of the dilution at a temperature comprised between 40° C. and a reflux temperature, for a period of time comprised between 1 and 4 hours;

d) cooling the suspension at a temperature comprised between 0 and 25° C.;

e) filtering it, optionally followed by one or more filter washings with an ester or alcohol or with an ester/alcohol mixture;

f) drying the wet solid product obtained in step e) at a temperature between 20 and 100° C.

The mixture of the two diastereoisomeric salts in step a) is in turn obtained according to a process comprising:

1) exposing a mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethylethoxy)carbonyl]amino]-5-[[imino(nitroamino)methyl]amino]-1-oxopentyl]-4-methylpiperidine-2-carboxylate (6) in an organic solvent, preferably selected from among an alcohol, an ester or a mixture thereof with HCl to a temperature comprised between 0° C. and the reflux temperature, preferably between 10 and 30° C.;

2) optionally, triggering a reaction of the solution with ethyl (2R,4R)-1-[(2S)-2-amino-5-[[imino(nitroamino)methyl]amino]-1-oxopentyl]-4-methylpiperidine-2-carboxylate compounded with HCl, solvated or unsolvated;

3) maintaining the mixture for a period of time comprised between 1 and 40 hours, preferably comprised between 3 and 20 hours, at a temperature comprised between 0° C. and the reflux temperature, preferably at a temperature comprised between 20 and 55° C., even more preferably for a period of time comprised between 3 and 6 hours at a temperature comprised between 40 and 50° C.;

said mixture of ethyl (2R,4R)-1-[(2S)-2-[[(1,1-dimethyletoxy)carbonyl]amino]-5[[imino(nitroamino)methyl]amino]-1-oxopentyl]-4-methylpiperidine-2-carboxylate (5) and ethyl (2S,4S)-1-[(2S)-2-[[(1,1-dimethylethoxy)carbonyl]amino]-5-[[imino(nitroamino)methyl]amino]-1-oxopentyl]-4-methylpiperidine-2-carboxylate (6) may contain water, preferably the water content is lower than 40% (weight/weight). In step a) or 1) of said process, said organic solvent and said mixture are used in a solvent volume/mixture weight ratio comprised between 5/1 and 25/1, preferably in a ratio comprised between 10/1 and 15/1. Said alcohol is selected from among ethanol, methanol, n-propanol, isopropanol, preferably it is ethanol. Said ester is preferably an alkyl acetate, preferably selected from among ethyl acetate, isopropyl acetate or butyl acetate, preferably it is isopropyl acetate. In step 1) an amount of HCl is used comprised between 1 and 4 equivalents, preferably between 2 and 3 equivalents, even more preferably about 3 equivalents. The product thus obtained has a content of ethyl (2S, 4S)-1-[(2S)-2-amino-5-[[imino(nitroamino)methyl]amino]-1-oxopenthyl]-4-methylpiperidine-2-carboxylate diastereoisomeric salt lower than 5% or lower than 2% or lower than 0.5%.

Purification

Purification may be carried out with the aim of obtaining a product with a very low or practically no content of (11) diastereoisomer. Such purification process comprises the following steps:

1) resuspending or dissolving said compound in an alcohol/ester mixture and heating at a temperature comprised between 20° C. and the reflux temperature, preferably a temperature comprised between 40 and 55° C. for a period of time comprised between 0.5 and 4 hours, preferably between 1 and 2 hours;

2) cooling said mixture at a temperature comprised between 0 and 25° C. and filtering it, optionally followed by one or more filter washings with an ester or alcohol or with an ester/alcohol mixture;

3) drying the wet solid product obtained in step 2) at a temperature between 20 and 100° C. obtaining ethyl (2R, 4R)-1-[(2S)-2-amino-5-[[imino(nitroamino)methyl]amino]-1-oxopentyl]-4-methylpiperidine-2-carboxylate compounded with HCl, solvated or unsolvated, having a content of ethyl (2S, 4S)-1-[(2S)-2-amino-5-[[imino(nitroamino)methyl]amino]-1-oxopenthyl]-4-methylpiperidine-2-carboxylate diastereoisomeric salt lower than 1% or lower than 0.5% or lower than 0.2%.

Said alcohol/ester mixture used in the purification step 1) is preferably constituted by absolute ethanol and ethyl acetate, preferably in a 1:1 ratio. In said step 2), said washing is repeated preferably twice using ethyl acetate.

Drying

The wet product obtained from the deprotection and crystallisation process or from the purification thereof is typically the dihydrochloride compound solvate. Drying at a relatively low temperature allows preserving the solvate. Using an alcohol such as ethanol in the isolation allows obtaining the ethanol solvate. Exposing such solvate to a temperature comprised between 40 and 50° C., preferably to 45° C. allows obtaining the ethyl (2R,4R)-1-[(2S)-2-amino-5-[[imino(nitroamino)methyl]amino]-1-oxopentyl]-4-methylpiperidine-2-carboxylate dihydrochloride ethanol solvate compound (4), having a content (weight/weight) of chlorides comprised between 11 and 15%, preferably comprised between 13.5 and 14.5% and an ethanol content of at least 0.5 mol/mol, more preferably comprised between 0.7 and 1 mol/mol. The ethanol content is typically analysed through NMR.

Drying the wet product obtained from the deprotection and crystallization process or from the purification thereof at a higher temperature, i.e. at a temperature comprised between 75 and 100° C. allows eliminating the solvent therefrom, obtaining the ethyl (2R,4R)-1-[(2S)-2-amino-5-[[imino(nitroamino)methyl]amino]-1-oxopentyl]-4-methylpiperidine-2-carboxylate dihydrochloride compound (3), having a content (weight/weight) of chlorides comprised between 12 and 16%. Preferably the drying is carried out under vacuum, for a period of time comprised between 4 and 48 hours, preferably for about 15 hours. The obtained compound 3, analysed through NMR, does not have a detectable signal due to ethanol.

Such compound 3 may also be obtained from the transformation of the dry solvate compound, for example from the compound 4 applying the same drying conditions, i.e. operating at a temperature comprised between 75 and 100° C.

Peptide Coupling

The mixture comprising 5 and 6, used for the deprotection process, is obtained through peptide coupling, starting from the racemic ethyl trans-(±)-4-methylpiperidine-2-carboxylate ester (7) or its hydrochloride 8 or, alternatively, from a mixture of ethyl (2R,4R)-4-methylpiperidine-2-carboxylate (9) and ethyl (2S,4S)-4-methylpiperidine-2-carboxylate (10), enriched with ethyl (2R,4R)-4-methylpiperidine-2-carboxylate (9). Said peptide coupling is carried out according to a process comprising:

a) dissolving 2-chloro-4,6-dimethoxy-1,3,5-triazine (CDMT) in an organic solvent;

b) adjusting the temperature of the solution obtained in step a) at a temperature comprised between −20 and +25° C., preferably between −10 and +10° C.;

c) adding N-methylmorpholine (NMM), wherein said adding operation is carried out maintaining the mixture at a temperature comprised between −10 and +25° C., subsequently letting said mixture react for a period of time comprised between 0.5 and 4 hours, preferably comprised between 1 and 2 hours;

d) adding N-Boc-N'-nitro-L-arginine and, optionally, an organic solvent, subsequently letting the mixture react for a period of time comprised between 0.5 and 4 hours, preferably for about 1 hour at a temperature comprised between −10 and +25° C.;

e) adding racemic ethyl trans-(±)-4-methylpiperidine-2-carboxylate ester (7) or its hydrochloride 8 or, alternatively, a mixture of ethyl (2R,4R)-4-methylpiperidine-2-carboxylate (9) and ethyl (2S,4S)-4-methylpiperidine-2-carboxylate (10), enriched with ethyl (2R,4R)-4-methylpiperidine-2-carboxylate (9) or pure ethyl (2R,4R)-4-methylpiperidine-2-carboxylate, letting the mixture react for a period of time comprised between 2 and 20 hours, at a temperature comprised between −10 and +25° C., preferably at 20° C.;

f) optionally, filtering the precipitate, followed by one or more panel washing operations with an organic solvent;

g) subsequent washings of the organic solution with aqueous solutions;

h) optionally, partial or total concentration of the organic phase by distillation at atmospheric or reduced pressure.

This allows obtaining a mixture 5/6 with an HPLC purity comprised between 95 and 99 which can be used as it is for the deprotection process. In said step a) said organic solvent is selected from among esters, ethers, chlorinated solvents, alkyl nitriles, preferably it is ethyl acetate, isopropyl acetate, butyl acetate, methyl terbutyl ether, isopropyl ether, butyl ether, tetrahydrofuran, 2-methyltetrahydrofuran, dichloromethane and acetonitrile. Said solvent is used in a solvent volume/weight ratio with respect to CDMT comprised between 5/1 and 25/1, preferably in a ratio comprised between 10/1 and 15/1. In said peptide coupling step d) N-Boc-N'-nitro-L-arginine is used in a molar ratio with respect to ethyl trans-(+)-4-methylpiperidine-2-carboxylate or hydrochloride thereof comprised between 0.8 and 1.3. The molar ratios of CDMT and NMM with respect to ethyl trans-(+)-4-methylpiperidine-2-carboxylate or hydrochloride thereof are comprised between 0.8 and 3. In said step e) about 1 mol equivalent of ester is added. The ester is used as a racemic or enriched or pure. The term pure ester is used to indicate a ratio of 9/10 equal to 97/3 or higher. In step g) in the aforementioned washings water is employed or basic aqueous solutions, acid aqueous solutions and saturated saline aqueous solutions are used; said basic aqueous solution is preferably 5% sodium bicarbonate, said acid solution is selected from among a 5% tartaric or citric acid solution or a diluted hydrochloric acid solution, said saturated aqueous saline solution is preferably water saturated with sodium chloride.

Synthesis of the Racemic 8 and/or Basic 7 HCl Ester.

The method for the synthesis of the base and/or hydrochloride (7, 8) ethyl trans-(±)-4-methylpiperidine-2-carboxylate, used in the peptide coupling process described above, comprises the following steps:

A) the trans-(±)-4-methylpiperidine-2-carboxylic hydrochloride acid (12), available from a synthetic process described for example in JP2003160560, is prepared as a solution with an organic polar solvent, maintaining said thermostated solution at a temperature comprised between 0 and 30° C.;

B) adding HCl to the solution obtained in A);

C) heating the mass obtained in step b) at a temperature comprised between 50° C. and reflux temperature, preferably at 70° C. and maintaining said temperature for a period of time comprised between 3 and 24 hours; preferably for 5-7 hours;

C') optionally, the mixture is filtered, washing the panel with an organic solvent and rejoining the washing solution with the first filtrate;

D) concentrating the mixture obtained in step C), or the rejoined filtrates obtained in step C') by distillation at reduced or atmospheric pressure, and optionally recovering it one or more times with an organic solvent and concentrating it at reduced or atmospheric pressure;

E) diluting the residue with an organic solvent;

F) optionally filtering said mixture obtained in step E) and obtaining hydrochloride salt 8;

F') alternatively, with the aim of obtaining the base 7, said mixture obtained in step E) is thermostated at a temperature comprised between about 0 and about 30° C. and then treated with basic aqueous solution obtaining a biphasic solution which is left under stirring for a period of time comprised between 30 and 120 minutes;

G') separating the organic phase from said biphasic solution, and optionally one or more further extractions of said aqueous phase with an organic solvent;

H') concentrating said organic phase and the two or more organic phases obtained in G') by distillation at reduced or atmospheric pressure, obtaining the ethyl trans-(±)-4-methylpiperidine-2-carboxylate product (7).

The GC purity for 8 and 7 is typically higher than 99.0%. The molar yield is typically comprised between 90 and 95%.

In said step A), said organic polar solvent is preferably absolute ethanol or denatured ethanol free of methanol or other alcohols. Said organic solvent is used in a volume/weight ratio of the trans-(±)-4-methylpiperidine-2-carboxylic hydrochloride acid (12) comprised between about 1/1 and about 10/1, preferably 5/1. In said step B) HCl is added as an HCl solution in ethanol or, in a further embodiment, as gaseous HCl by bubbling, using 1-3 equivalents of HCl, preferably about 2 equivalents. In said steps D), E), F), F'), G') and H') the organic solvent is selected from among esters, ethers, chlorinated solvents, alkyl nitriles, aromatic hydrocarbons and ketones, and preferably said organic solvent is selected from among ethyl acetate, isopropyl acetate, butyl acetate, methyl terbutyl ether, isopropyl ether, butyl ether, 2-methyltetrahydrofuran, dichloromethane, toluene, methyl ethyl ketone.

In an alternative embodiment, the method of synthesis of ethyl trans-(±)-4-methylpiperidine-2-carboxylate (7) comprises the following steps:

A) the trans-(±)-4-methylpiperidine-2-carboxylic hydrochloride acid (12) is prepared in a solution with an organic polar solvent maintaining said thermostated solution at a temperature comprised between 0 and 30° C.;

B) adding $SOCl_2$ to the solution obtained in step a) maintaining the temperature comprised between 0 and 30° C.;

C) heating the mass obtained in step b) at a temperature comprised between 50° C. and reflux temperature, preferably at reflux temperature and maintaining said temperature for a period of time comprised between 2 and 24 hours; preferably for 2-4 hours;

D) concentrating the mixture by distillation at reduced or atmospheric pressure, and optionally recovering it one or more times with an organic solvent and concentrating it at reduced or atmospheric pressure;

E) diluting the residue with an organic solvent;

F') adjusting the temperature comprised between about 0 and about 30° C. and subsequently treating it with basic aqueous solution obtaining a biphasic solution which is left under stirring for a period of time comprised between 30 and 120 minutes;

G') separating the organic phase from said biphasic solution, and optionally one or more further extractions of said aqueous phase with an organic solvent;

H') concentrating said organic phase and the two or more organic phases obtained in G') by distillation at reduced or atmospheric pressure, obtaining the ethyl trans-(±)-4-methylpiperidine-2-carboxylate product (7) with a GC purity typically higher than 99.0%. The molar yield is typically comprised between 90 and 95%.

In said step A) said organic polar solvent is selected from among ethanol, preferably absolute ethanol or denatured ethanol free of methanol or other alcohols. Said ethanol is used in a volume/weight ratio of the trans-(±)-4-methylpiperidine-2-carboxylic hydrochloride acid (12) comprised between about 1/1 and about 10/1, preferably 5/1. In said step B) SOCl2 is added using 0.5-0.9 equivalents of SOCl2, preferably about 0.7 equivalents. In said step D), E), F'), G') and H') the organic solvent is selected from among ester, ether, chlorinated solvents, alkyl nitriles, aromatic hydrocarbons and ketones, and preferably said organic solvent is selected from among ethyl acetate, isopropyl acetate, butyl acetate, methyl terbutyl ether, isopropyl ether, butyl ether, 2-methyltetrahydrofuran, dichloromethane, toluene, methyl ethyl ketone.

Starting from the racemic ester 8/7 obtained as described, the ethyl (2R,4R)-1-[(2S)-2-amino-5-[[imino(nitroamino) methyl]amino]-1-oxopentyl]-4-methylpiperidine-2-carboxylate product compounded with HCl, solvated or unsolvated is attained with an HPLC area purity as the sum of the two diastereoisomers higher than 99%. The molar yield from racemic ester 8/7 is of about 30-45%.

Should one decide to proceed with the peptide coupling, the deprotection and the isolation of the ethyl (2R,4R)-1-[(2S)-2-amino-5-[[imino(nitroamino)methyl]amino]-1-oxopentyl]-4-methylpiperidine-2-carboxylate product compounded with HCl, solvated or unsolvated, starting from an enriched or pure ester, said enriched or pure ester (9) is preferably obtained with the method that follows and comprising the following steps:

i) Ethyl trans-(±)-4-methylpiperidine-2-carboxylate (7) is reacted with tartaric acid in a mixture of organic solvents, preferably acetone and absolute ethanol, heated at a temperature comprised between 30 and 50° C., preferably at about 40° C., for a period of time comprised between 15 and 60 minutes, preferably for about 30 minutes, then it is cooled at about 20° C.;

ii) to the mixture in i) the trigger prepared separately is added, by suspending ethyl (2R,4R)-4-methyl-2-piperidinecarboxylate L-tartrate (13) in a mixture of organic solvents, preferably acetone and absolute ethanol, stirring for at least 1 hour, together with a mixture of acetone/absolute ethanol;

iii) after about 5 hours at about 20° C. the suspension obtained in step ii) is filtered and it is washed one or more times with acetone obtaining, after drying, a mixture of ethyl (2R,4R)-4-methyl-2-piperidinecarboxylate L-tartrate (13) diastereoisomeric salts and ethyl (2S,4S)-4-methyl-2-piperidinecarboxylate L-tartrate (14), enriched in 13;

iii') alternatively, with the aim of obtaining the pure diastereoisomeric salt the diastereoisomeric salt enriched with an acetone/absolute ethanol mixture is suspended at about 60° C. for about 30 min. The suspension is cooled at 35° C., it is filtered and washed one or more times with acetone obtaining, after drying, the pure ethyl (2R,4R)-4-methyl-2-piperidinecarboxylate L-tartrate (13) diastereoisomeric salt;

iv) an organic solvent, preferably ethyl acetate, and water are added to the enriched compound 13 obtained in step iii) or pure compound obtained in step iii');

v) after cooling at about 15° C. a basic aqueous solution is added in about 5 minutes and the biphasic solution obtained is left under stirring at about 20° C. for about 1 hour;

vi) after separating the phases, the aqueous phase is extracted once again and the two organic phases are concentrated by distillation at reduced pressure, obtaining the enriched or pure ester as a free base.

The described method leads to a product with an ethyl (2R,4R)-4-methyl-2-piperidinecarboxylate (9)/ethyl (2S,4S)-4-methyl-2-piperidinecarboxylate (10) ratio of about 87/13 for the enriched ester, or 97/3 or higher for the pure ester.

Proceeding with the peptide coupling, the deprotection and the isolation of the ethyl (2R,4R)-1-[(2S)-2-amino-5-[[imino(nitroamino)methyl]amino]-1-oxopentyl]-4-methyl-piperidine-2-carboxylate product compounded with HCl, solvated or unsolvated, starting from the enriched ester 9/10, in a ratio comprised between 84/15 and 87/13, the HPLC purity as the sum of the two diastereoisomers is higher than 99.5%, with a diasteroisomer content 11 not desired below 1.5%. The molar yield starting from the enriched ester 9/10 is of 65-90%.

Proceeding with the peptide coupling, the deprotection and the isolation of the ethyl (2R,4R)-1-[(2S)-2-amino-5-[[imino(nitroamino)methyl]amino]-1-oxopentyl]-4-methyl-piperidine-2-carboxylate product compounded with HCl, solvated or unsolvated, starting from pure ester, wherein the term pure ester is used to indicate a ratio 9/10 equal to about 97/3 or higher, the HPLC purity as sum of the two diastereoisomers 4 and 11 is higher than 99.5%, with a diasteroisomer content 11 not desired lower than 0.2%. The molar yield starting from the pure ester 9/10 (ratio equal to about 97/3) is of 65-90%.

The process described in the present invention, allowing the use of the racemic ester 7, offers considerable advantages with respect to the known art, leading to a short and direct synthesis of the intermediate 4 or 3. In particular, the resolution of the ester 7 or the 4-methyl pipecolic acid 12 are not required to obtain pure ester. A purification of the ester through, for example, chromatography or an enantioselective synthesis thereof is not even required. Thus, the direct process represents a considerable improvement of the prior art with doubled yields with respect to the process including the resolution and thus leading to an increased process productivity.

Furthermore, the organic solvent used in the esterification, coupling and deprotection steps may be the same, thus avoiding the necessity to remove the solvent.

The process described in the present invention avoids the use of toxic solvents, by way of example, in the esterification process, the use of thionyl chloride may be avoided, contrary to what is indicated in the prior art. Furthermore, in the coupling process, the isobutyl chloroformate—a toxic substance which leads to the formation of a cyclic by-product and requires operating at lower temperatures (about −20° C.)—employed in the prior art is not used. Vice versa, CDMT is easily available, it reveals low toxicity and it also allows operating at a temperature of about 15-20° C.

Ethyl (2R,4R)-1-[(2S)-2-amino-5-[[imino(nitroamino)methyl]amino]-1-oxopentyl]-4-methylpiperidine-2-carboxylate compounded with HCl tends, in the presence of many solvents, to form a rubber. The mixture of solvents described herein instead allows obtaining a crystalline solid easy to isolate through filtration. Furthermore, the solvent ratio used allows, surprisingly, the almost complete elimination of the unwanted diasteroisomer 11 in mother liquors. The diasteroisomer 11 content in the HPLC area is maintained at levels lower than 5% and typically lower than 2%. Furthermore, the product 4 thus obtained does not have or is almost free of impurities except from diasteroisomer 11 contrary to the indicated levels.

The isolated compound 4 is a dihydrochloride ethanol solvate. The same is much less soluble in ethanol with respect to monohydrochloride, thus allowing the use of a large excess of ethanol in the isolation mixture.

Furthermore, the method proposed for obtaining enriched or pure ester 9 is optimized with respect to what is described in the prior art in the triggering step, given that surprising advantages—even in terms of reproducibility were observed by activating the trigger separately, by preparing a suspension of 13 with a minimum purity of 13/14 equal to 85/15 and waiting for at least 1 hour before adding the same to the solution of the resolution. Also the provided process temperatures of about 20° C., with respect to the 3-10° C. described in the prior art, allow isolating the desired sufficiently pure diastereoisomeric salt 13 even before the precipitation of the unwanted salt 14; this allows obtaining a product enriched in 13 by about 85-87% with a molar yield of about 28-30%.

The following examples are provided purely by way of example and they shall not be deemed restrictive with respect to the present invention in any manner whatsoever.

EXAMPLES

Example 1: Synthesis of the trans-(±)-4-methylpiperidine-2-carboxylic Hydrochloride Acid Salt (12)

1A: Synthesis of 4-methyl-2,3,4,5-tetrahydropyridine (15)

In a reactor 126 g of glacial acetic acid and 186 ml of water are introduced; the solution is cooled at 0÷10° C. and maintaining such temperature in about 2 hours, 200 g of 4-methylpiperidine are added. The reaction mixture is heated at 20° C. and the resulting solution is added, slowly (at least 1 hour), to a 3000 ml solution of aqueous sodium hypochlorite 15 V, pre-cooled at 0° C. The mixture thus obtained is left under stirring for 1 hour at 0÷10° C., then brought to 20° C. and extracted using 1600 ml of dichloromethane and subsequently using another 500 ml of dichloromethane. 380 ml of a 30% sodium methylate solution in methanol are thus added to the organic phases slowly (from 1 to 4 hours) at 0÷10° C. The obtained suspension is then brought to 20° C. and maintained at such temperature for one night. 500 ml of water are added and the phases are separated. The organic phase is subsequently washed using 400 ml of 10% NaOH and preserved at ambient temperature for the subsequent step.

The estimated yield, on 2018 g of solution, containing about 9% of the product, is of about 182 g of 4-methyl-2, 3,4,5-tetrahydropyridine equivalent to 94% molar.

1B: Synthesis of 4-methylpiperidine-2-carbonitrile (16)

In a glass flask 2000 g of 4-methyl-2,3,4,5-tetrahydropyridine solution in dichloromethane (equal to 180 g) obtained from step 1A and 360 ml of water are introduced. The mixture thus obtained is cooled at T<10° C. and at this temperature—drop by drop—, over a period of time of 1 hour, 175 ml of 37% HCl are added. The obtained mixture is kept under stirring at 0÷10° C. for 30 minutes, then the two phases are separated and the aqueous phase containing 4-methyl-2,3,4,5-tetrahydropyridine hydrochloride is stored for the subsequent part of the process. Simultaneously in another glass reactor 130 g of sodium cyanide (1.4 equivalents), 540 ml of water and 900 ml of dichloromethane are introduced. The obtained mixture is cooled at 0° C. and the aqueous solution of 4-methyl-2,3,4,5-tetrahydropyridine hydrochloride obtained previously is percolated at this temperature, over a period of time of about 4 hours. Upon completing the adding operation, the mass is brought to 20° C. and kept under stirring throughout the night. The organic phase is separated and then washed using 500 ml of 5% NaOH and subsequently twice using 500 ml of water and lastly concentrated to residue at reduced pressure.

184 g of 4-methylpiperidine-2-carbonitrile are obtained as a reddish oily residue, with an estimated yield of 74%.

1C: Synthesis of the trans-(±)-4-methylpiperidine-2-carboxylic Hydrochloride Acid Salt (12)

In a reactor 160 g of 4-methylpiperidine-2-carbonitrile obtained in step 1B are introduced. To this 480 ml of 37% HCl are added under stirring, maintaining the temperature below 20° C. The mixture thus obtained is brought to 60° C. and maintained at such temperature during the night, then cooled at 0° C. and maintained at such temperature for 3.5 hours. The precipitate is filtered and the panel is washed using 50 ml of acetone, then the crystalline solid is dried in an oven at a reduced pressure at 50° C.

145 g of trans-(±)-4-methylpiperidine-2-carboxylic hydrochloride acid are obtained. 70% yield.

Example 2: Synthesis of ethyl trans-(±)-4-methylpiperidine-2-carboxylate Base and Hydrochloride 2A: Synthesis of ethyl trans-(±)-4-methylpiperidine-2-carboxylate (7) with Method 1 (Ethanol/HCl)

In a reactor 800 g of trans-(±)-4-methylpiperidine-2-carboxylic hydrochloride acid containing ammonium chloride, corresponding to 464 g of 100% acid hydrochloride, and 850 ml of absolute ethanol are introduced. The obtained solution is thermostated at 20° C. and at this temperature 1,343 g of a 14.2% HCl solution in ethanol were added. The mass is brought to 70° C. and maintained at such temperature for 6 hours, then brought to 20° C. and left under stirring for a night. The mixture is concentrated by distillation at reduced pressure then recovered 3 times with 465 ml of ethyl acetate and concentrated at reduced pressure. The oily residue is diluted with 2,320 ml of ethyl acetate, the solution is cooled at 10÷20° C. and then treated with a solution of 418 g of potassium carbonate in 1,400 ml of water. The obtained biphasic solution was left under stirring at 20° C. for 90 minutes, then the phases are separated and the aqueous phase is extracted once again using 900 ml of ethyl acetate, the two organic phases are concentrated by distillation at reduced pressure obtaining a total of 413 g (403.4 g titre-calculated) of ethyl trans-(±)-4-methylpiperidine-2-carboxylate with an average GC purity of 99.3%. Molar yield: 91%.

2B: Synthesis of ethyl trans-(±)-4-methylpiperidine-2-carboxylate (7) with Method 2 (SOCl$_2$)

In a reactor 86 g of trans-(±)-acid 4-methylpiperidine-2-carboxylic hydrochloride containing ammonium chloride, corresponding to 50 g of 100% acid hydrochloride and 250 ml of absolute ethanol are introduced. The obtained solution is thermostated at 0±10° C. and at this temperature 15 ml of SOCl$_2$ (0.7 equivalents) are added. The mass is gradually heated up to reflux and maintained at such temperature for 3 hours, then brought to 20° C. and left under stirring for a night. The mixture is concentrated by distillation at reduced pressure then recovered 3 times with 50 ml of ethyl acetate and concentrated at reduced pressure. The oily residue is diluted with 250 ml of ethyl acetate, the solution is cooled at 0÷10° C. and treated with a solution of 45 g of potassium carbonate in 150 ml of water. The obtained biphasic solution is left under stirring at 20° C. for 1 hour, then the phases are separated, the aqueous phase is extracted once again using 100 ml of ethyl acetate, the two organic phases are concentrated by distillation at reduced pressure separately leading to respectively obtaining 47 g and 3.5 g of ester, equal to a total of 50.5 g (43.7 g titre-calculated) with an average purity of 99.5%. Molar yield: 92%.

2C: Synthesis of the ethyl trans-(±)-4-methylpiperidine-2-carboxylate Hydrochloride (8)

In a reactor 86.5 g of trans-(±)-acid 4-methylpiperidine-2-carboxylic hydrochloride containing ammonium chloride, corresponding to 50 g of 100% acid hydrochloride, and 250 ml of absolute ethanol are introduced. The obtained solution is thermostated at 0° C. and at this temperature, by bubbling, 20.5 g of HCl gas are added. The mass is brought to 70° C. and maintained at such temperature for 6 hours, then cooled at 20° C. and left under stirring for a night. The formed inorganic salts are filtered, and the panel is washed with 25 ml of absolute ethanol; the washing was rejoined with the first filtrate. The mixture is concentrated by distillation at reduced pressure then recovered twice with 50 ml of isopropyl acetate and concentrated at reduced pressure. The oily residue was diluted with 100 ml of isopropyl acetate once again filtered, obtaining 137 g of solution with a 39.5% titre, equal to 54.1 g of ethyl trans-(±)-4-methylpiperidine-2-carboxylate hydrochloride. Molar yield: 94%.

Example 3: Synthesis of ethyl (2R,4R)-1-[(2S)-2-amino-5-[[imino(nitroamino)methyl]amino]-1-oxopentyl]-4-methylpiperidine-2-carboxylate Dihydrochloride Solvated by Ethanol (4)

3A: Synthesis of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) from Racemic Ester (7) with 0.9 eq. of N-Boc-N'-nitro-L-arginine In a reactor 12.1 g of 2-chloro-4,6-dimethoxy-1,3,5-triazine (CDMT) and 120 ml of ethyl acetate are introduced. The obtained solution is cooled at −10° C. and at this temperature 12.7 g of N-methylmorpholine (NMM) are slowly added obtaining a suspension. After 1.5 hours 20 g of N-Boc-N'-nitro-L-arginine and 24 ml of ethyl acetate are added. After another hour 12.6 g of ethyl trans-(±)-4-methylpiperidine-2-carboxylate (7) are added, 93.4% titre corresponding to 11.8 g. After 2 hours the temperature is brought to 0° C. and the reaction mixture is kept under stirring at such temperature throughout the night. The suspension is filtered and the panel washed twice with 10 ml of ethyl acetate. The organic solution is washed using 160 ml of a 5% aqueous sodium bicarbonate solution, 100 ml of saturated sodium chloride aqueous solution, 100 ml of a 5% tartaric acid solution and 100 ml of saturated sodium chloride aqueous solution. The organic phase is concentrated by distillation at reduced pressure obtaining 26.4 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereomers as a rubber-like solid. HPLC purity (as the sum of the two diastereoisomers): 97.9%. The solid is used as it is in the subsequent step.

3B: Synthesis of ethyl (2R,4R)-1-[(2S)-2-amino-5-[[imino(nitroamino)methyl]amino]-1-oxopentyl]-4-methylpiperidine-2-carboxylate Dihydrochloride Ethanol Solvate (4)

In a reactor 26 g of the mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) (as obtained in the example 3A) and 130 ml of absolute ethanol are introduced. The obtained solution is cooled at 15° C. and at this temperature 6 g of gaseous HCl were slowly added maintaining the temperature between 20-30° C. After 1 hour the solution was triggered using a few mg of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4) and left at 15° C. throughout the night. The suspension is diluted with 36 ml of absolute ethanol and heated at 50° C. At such temperature 208 ml of ethyl acetate are added. After 1.5 hours the mixture is cooled at 20° C. and filtered washing the panel on the filter twice using 25 ml of ethyl acetate. The solid product is dried in an oven under vacuum at 45° C. obtaining 10.5 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 2% of the corresponding dihydrochloride ethyl (2S,4S)-1-[(2S)-2-amino-5-[[imino(nitroamino)methyl]amino]-1-oxopentyl]-4-methylpiperidine-2-carboxylate (11) diastereoisomer.

HPLC purity area as the sum of the two diastereoisomers: 99.9% (the ratio 4/11 is 98/2). Molar yield: 36% from ethyl trans-(±)-4-methylpiperidine-2-carboxylate (7).

3C: Synthesis of (5) and (6) from Racemic Ester (7) with 1.2 Equivalents of N-Boc-N'-Nitro-L-Arginine In a reactor 18.7 g of CDMT and 196 ml of ethyl acetate are introduced. The obtained solution is cooled at −10° C. and at this temperature in about 20 min 11.2 g of NMM are slowly added obtaining a suspension. After 1.5-2 hours 32.7 g of N-Boc-N'-nitro-L-arginine and 40 ml of ethyl acetate are added. After another hour there are added 15.3 g of ethyl trans-(±)-4-methylpiperidine-2-carboxylate (7) (95.7% titre corresponding to 14.64 g) in about 30 min. After 2 hours at −10° C., the temperature is brought to 20° C. in 1 hour and the reaction mixture is kept under stirring at such temperature throughout the night. The suspension is filtered and the panel washed twice with 30 ml of ethyl acetate. The organic solution is washed using 120 ml of a 5% aqueous sodium bicarbonate solution, 120 ml of 5% hydrochloric acid and 120 ml of saturated sodium chloride aqueous solution. The organic phase is concentrated by distillation at low pressure obtaining 46.3 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereomers as a rubber-like solid.

HPLC purity (as the sum of the two diastereoisomers): 93.3%. The solid is used as it is in the subsequent step.

3D: Synthesis of ethyl (2R,4R)-1-[(2S)-2-amino-5-[[imino(nitroamino)methyl]amino]-1-oxopentyl]-4-methylpiperidine-2-carboxylate Dihydrochloride Solvated by Ethanol (4)

In a reactor 46 g of the mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) (as obtained in the example 3C) and 256 ml of absolute ethanol and 80 ml of ethyl acetate are introduced. The obtained solution is cooled at 15° C. and at this temperature 9.3 g of gaseous HCl were added slowly maintaining the temperature at 20° C. The solution was triggered with 20 mg of (2R,4R)-1-[(2S)-2-amino-5-[[imino(nitroamino)methyl]-amino]-1-oxopentyl]-4-methylpiperidine-2-carboxylate, dihydrochloride ethanol solvate (4) and left at 25° C. throughout the night. The suspension is heated at 50° C. and at such temperature 240 ml of ethyl acetate are added. After about 1.5 hours the mixture is cooled at 20° C. and filtered washing the panel on the filter twice with 40 ml of ethyl acetate. The solid product is dried in an oven under vacuum at 45° C. obtaining 17.6 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 1.4% of the corresponding dihydrochloride ethyl (2S,4S)-1-[(2S)-2-amino-5-[[imino(nitroamino)methyl]amino]-1-oxopentyl]-4-methylpiperidine-2-carboxylate (11) diastereoisomer.

HPLC purity area as the sum of the two diastereoisomers: 99.9% (the 4/11 ratio is 98.6/1.4). The chloride content is 13.7%. Molar yield: 42% from ethyl trans-(±)-4-methylpiperidine-2-carboxylate (7).

3E: Synthesis of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) from Racemic Ester ethyl trans-(±)-4-methylpiperidine-2-carboxylate Base (7) (Reaction at a Temperature of 15-20° C.)

In a reactor 25 g of CDMT and 263 ml of ethyl acetate are introduced. The obtained solution is cooled at 15-20° C. and 15 g of NMM are slowly added at this temperature in about 20 minutes obtaining a suspension. After 1.5 hours 44 g of N-Boc-N'-nitro-L-arginine and 50 ml of ethyl acetate are added. After another hour 28.9 g of ethyl trans-(±)-4-methylpiperidine-2-carboxylate (7) (67.7% titre corresponding to 19.6 g) in about 20 minutes are added. The reaction mixture is kept under stirring at 20° C. throughout the night. The suspension is filtered and the panel washed twice using 40 ml of ethyl acetate. The organic solution is washed using 160 ml of a 5% aqueous sodium bicarbonate solution, 160 ml of 5% hydrochloric acid and 160 ml of saturated sodium chloride aqueous solution. The organic phase is concentrated by distillation at low pressure obtaining 55 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers.

HPLC purity (as the sum of the two diastereoisomers): 95.7%. The product is used as it is in the subsequent step.

3F: Synthesis of ethyl (2R,4R)-1-[(2S)-2-amino-5-[[imino(nitroamino)methyl]amino]-1-oxopentyl]-4-methylpiperidine-2-carboxylate Dihydrochloride Solvated by Ethanol (4)

55 g of a mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) (as obtained in the example 3E), 343 ml of absolute ethanol and 108 ml of ethyl acetate are introduced in a reactor. The obtained solution is cooled at 10° C. and at this temperature 12.5 g of gaseous HCl were added slowly maintaining the temperature below 20° C. The solution is heated at 50° C. and a precipitate is formed without triggering. After about one hour it is diluted with 320 ml of ethyl acetate. After about 5 hours the mixture is cooled at 20° C. and filtered washing the panel on the filter twice using 30 ml of ethyl acetate. The solid product is dried in an oven under vacuum at 45° C. obtaining 26 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 2.6% of the corresponding dihydrochloride ethyl (2S,4S)-1-[(2S)-2-amino-5-[[imino(nitroamino)methyl]amino]-1-oxopentyl]-4-methylpiperidine-2-carboxylate (11) diastereoisomer.

HPLC area purity as the sum of the two diastereoisomers: 99.5% (the ratio 4/11 is 97.4/2.6). The chloride content is 13.6%. Molar yield: 46% from ethyl trans-(±)-4-methylpiperidine-2-carboxylate (7).

3G: Synthesis of (5) and (6) from Racemic Ester (7)

50 g of CDMT and 525 ml of ethyl acetate are introduced in a reactor. The obtained solution is cooled at 0-5° C. and 30 g of NMM are slowly added at this temperature obtaining a suspension. After 1.5 hours 87.8 g of N-Boc-N'-nitro-L-arginine and 95 ml of ethyl acetate are added. After another hour 41.1 g of ethyl trans-(±)-4-methylpiperidine-2-carboxylate (7) (94.8% titre corresponding to 38.9 g) are added. After 2 hours at 0-5° C., the temperature is brought to 20° C. and the reaction mixture is kept under stirring at such temperature throughout the night. 470 ml of water are added to the suspension. Heating is carried out at 35° C. and it is left under stirring for 15 minutes. After separating the phases, the organic phase is washed using 320 ml of a 5% aqueous sodium bicarbonate solution, 320 ml of 5% hydrochloric acid and 320 ml of saturated sodium chloride aqueous solution. The organic phase is concentrated by distillation at low pressure obtaining 114 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers.

HPLC purity (as the sum of the two diastereoisomers): 97.1%.

3H: Synthesis of (4)

Starting from 46 g (100%) of 7 and applying the procedure described in the example 3C, after the aqueous washings a mixture of 5 and 6 in about 900 ml acetate of ethyl acetate is obtained. About 140 ml of solvent are distilled under atmospheric pressure at a temperature of 72° C. and the movement of water is controlled (KF is 3.6%). The solution is cooled at a temperature of 5° C., then adding 805 ml of ethyl acetate. 29.4 g of gaseous HCl are slowly added maintaining the temperature below 30° C. The solution was triggered with 20 mg of (2R,4R)-1-[(2S)-2-amino-5-[[imino(nitroamino)methyl]-amino]-1-oxopentyl]-4-methylpiperidine-2-carboxylate, dihydrochloride ethanol solvate (4) and left at 20° C. throughout the night. The suspension is heated at 50° C. and at such temperature 240 ml of ethyl acetate are added. After about 2 hours the mixture is cooled at 20° C. and filtered washing the panel on the filter twice using 124 ml of ethyl acetate. The solid product is dried in an oven under vacuum at 45° C. obtaining 54 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 3.9% of the corresponding ethyl (2S,4S)-1-[(2S)-2-amino-5-[[imino(nitroamino)methyl]amino]-1-oxopentyl]-4-methylpiperidine-2-carboxylate dihydrochloride (11) diastereoisomer.

HPLC area purity as the sum of the two diastereoisomers: 99.8% (the ratio 4/11 is 96.1/3.9). The chloride content is 13.2%. Molar yield: 41% from ethyl trans-(±)-4-methylpiperidine-2-carboxylate (7).

3I: Synthesis of (5) and (6) from Racemic Ester HCl (8)

35 g of CDMT and 345 ml of ethyl acetate are introduced in a reactor. The obtained solution is cooled at −10° C. and at this temperature 40.3 g of NMM are slowly added obtaining a suspension. After 1 hour 57.8 g of N-Boc-N'-nitro-L-arginine and 70 ml of ethyl acetate are added. After another hour 105 g of a solution of ethyl trans-(±)-4-methylpiperidine-2-carboxylate hydrochloride (8) in isopropyl acetate are added (39.5% titre corresponding to 41.5 g of 100% ethyl trans-(±)-4-methylpiperidine-2-carboxylate hydrochloride). After 2 hours the temperature is brought to 20° C. and the reaction mixture kept under stirring at such temperature throughout the night. The suspension is filtered and the panel is washed twice using 100 ml of ethyl acetate. The organic solution is washed twice using 100 ml of a 5% aqueous sodium bicarbonate solution, 100 ml of saturated sodium chloride water, 100 ml of a 5% tartaric acid solution and 100 ml of saturated sodium chloride water.

The organic phase is concentrated by distillation at low pressure obtaining 77.8 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers as oil.

HPLC area purity as the sum of the two diastereoisomers: 98.0%. The product is used as it is in the subsequent step.

3K: Synthesis of (4)

77.5 g of the mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) as obtained in step 3I, 495 ml of absolute ethanol and 155 ml of ethyl acetate are introduced in a reactor. The obtained solution is cooled at 10° C. and at this temperature 17.9 g of gaseous HCl are slowly added maintaining the temperature between 10 and 30° C. After 40 minutes the solution is triggered with 50 mg of ethyl (2R,4R)-1-[(2S)-2-amino-5-[[imino(nitroamino)methyl]-amino]-1-oxopentyl]-4-methylpiperidine-2-carboxylate, dihydrochloride ethanol solvate (4) and left at 20° C. for about 40 hours. At such temperature 465 ml of ethyl acetate are added. The suspension is heated at 50° C. After 1.5 hours the suspension is cooled at 20° C. and the precipitate filtered washing the panel twice using 70 ml of ethyl acetate. The solid product is dried in an oven under vacuum at 45° C. obtaining 27.5 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 2% of the ethyl (2S,4S)-1-[(2S)-2-amino-5-[[imino(nitroamino)methyl]amino]-1-oxopentyl]-4-methylpiperidine-2-carboxylate dihydrochloride (11) diastereoisomer; (the 4/11 ratio is 98/2).

HPLC area purity as the sum of the two diastereoisomers: 99.0%. Molar yield: 28% from ethyl trans-(±)-4-methylpiperidine-2-carboxylate hydrochloride (8).

3L: Synthesis of (5) and (6)

28.3 g of N-Boc-N'-nitro-L-arginine and 450 ml of THF are introduced in a reactor. The obtained suspension is cooled at −20° C. and 9 g of triethylamine and 12.2 g of isobutyl chloroformate are added. After 10 minutes 16.4 g of ethyl trans-(±)-4-methylpiperidine-2-carboxylate (7) (92.7% titre corresponding to 15.2 g) are added maintaining at −20° C. After 10 mins the temperature is gradually raised to ambient temperature. The organic phase is concentrated by distillation at low pressure and the residue is diluted with 400 ml of ethyl acetate. The mixture is washed using 200 ml of water, 100 ml of a 5% aqueous sodium bicarbonate solution, 100 ml of a 5% solution of citric acid and 200 ml of water.

The organic phase is concentrated by distillation at low pressure obtaining 34 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers as solid. HPLC purity (as the sum of the two diastereoisomers): 73%.

The solid is used as it is in the subsequent step.

3M: Synthesis of (4)

33 g of the mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) as obtained in 3L and 211 ml of absolute ethanol are introduced in a reactor. The obtained solution is cooled at 20° C. and at this temperature 7.6 g of gaseous HCl were slowly added maintaining the temperature between 20-30° C. The solution was triggered with 20 mg of (2R,4R)-1-[(2S)-2-amino-5-[[imino(nitroamino)methyl]-amino]-1-oxopentyl]-4-methylpiperidine-2-carboxylate, dihydrochloride hydrochloride ethanol solvate (4) and left at 20° C. throughout the night. The suspension is heated at 50° C. At such temperature 198 ml of ethyl acetate are added. After 1.5 hours the mixture is cooled at 20° C. and filtered washing the panel on the filter twice with 50 ml of ethyl acetate. The solid product is dried in an oven under vacuum at 45° C. obtaining 5.5 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 0.6% of the corresponding dihydrochloride ethyl (2S,4S)-1-[(2S)-2-amino-5-[[imino(nitroamino)methyl]amino]-1-oxopentyl]-4-methylpiperidine-2-carboxylate (11) diastereoisomer.

HPLC purity area as the sum of the two diastereoisomers: 99.9% (the ratio 4/11 is 99.4/0.6). The chloride content is 14.1%. Molar yield: 13% from ethyl trans-(±)-4-methylpiperidine-2-carboxylate (7).

3N: Synthesis of (5) and (6) from Enriched Ester (9)/(10) (87/13)

27.9 g of CDMT and 276 ml of ethyl acetate are introduced in a reactor. The obtained solution is cooled at −10°

C. and at this temperature 16.8 g of NMM are slowly added obtaining a suspension. After 40 min 46 g of N-Boc-N'-nitro-L-arginine and 55 ml of ethyl acetate are added. The temperature is brought to −5° C. and after 1.5 hours there 27 g of a mixture of ethyl (2R,4R)-4-methylpiperidine-2-carboxylate and ethyl (2S,4S)-4-methylpiperidine-2-carboxylate (9/10) in an 87/13 ratio (from example 4C) were added. After 2 hours the reaction mixture is heated at 20° C. and kept under stirring at such temperature throughout the night.

The suspension is filtered and the panel is washed with 184 ml of ethyl acetate. The organic solution is washed using 276 ml of a 5% sodium bicarbonate aqueous solution, 276 ml of hydrochloric acid 2N and 276 ml of saturated sodium chloride water.

The organic phase was concentrated by distillation at reduced pressure obtaining 71 g of a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers as oil (ratio 86/14).

HPLC purity area as the sum of the two diastereoisomers: 94.6%. The product is used as it is in the subsequent step.

3O: Synthesis of (4)

71 g of the mixture of two diastereoisomers ethyl (2R, 4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) (obtained in the example 3N) and 455 ml of absolute ethanol are introduced in a reactor. The obtained solution is cooled at 10° C. and at this temperature 16.5 g of gaseous HCl are slowly added maintaining the temperature between 15 and 30° C. After 1 hour the solution is triggered with a few mg of (2R,4R)-1-[(2S)-2-amino-5-[[imino(nitroamino)methyl]-amino]-1-oxopentyl]-4-methylpiperidine-2-carboxylate, dihydrochloride hydrochloride ethanol solvate (4) and left at 20° C. throughout the night. The suspension is diluted with 426 ml of ethyl acetate and heated at 50° C. After 1.5 hours the suspension is cooled at 20° C. and the precipitate is filtered washing twice with 70 ml of ethyl acetate. The solid product is dried in an oven under vacuum at 45° C. obtaining 51 g of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4). The product contains 1.1% of the dihydrochloride ethyl (2S,4S)-1-[(2S)-2-amino-5-[[imino(nitroamino)methyl]amino]-1-oxopentyl]-4-methylpiperidine-2-carboxylate (11) diastereoisomer; (the ratio 4/11 is 98.9/1.1).

HPLC purity area as the sum of the two diastereoisomers: 100%. Molar yield: 66%, starting from a mixture of ethyl (2R,4R)-4-methylpiperidine-2-carboxylate and ethyl (2S,4S)-4-methylpiperidine-2-carboxylate (9/10) with a ratio of 85/15.

3P: Synthesis of (5)/(6) from Pure Ester (9)/(10) (98/2)

33.7 g of CDMT and 334 ml of ethyl acetate are introduced in a reactor. The obtained solution is cooled at −10° C. and at this temperature 20.3 g of NMM are slowly added obtaining a suspension. After 40 minutes 55.6 g of N-Boc-N'-nitro-L-arginine and 117 ml of ethyl acetate are added. After about 1.5 hours 32.7 g of a mixture of ethyl(2R,4R)-4-methylpiperidine-2-carboxylate and ethyl (2S,4S)-4-methylpiperidine-2-carboxylate (9/10) with a ratio of 97.7/2.3 (from example 4D) are added. After about 2.5 hours the reaction mixture is brought to 10° C. and kept under stirring at such temperature throughout the night. The suspension is filtered and the panel is washed with 222 ml of ethyl acetate. The organic solution is washed using 334 ml of a 5% sodium bicarbonate aqueous solution, 334 ml of hydrochloric acid 2N and 334 ml of saturated sodium chloride water.

The organic phase is concentrated by distillation at reduced pressure obtaining 85 g of a mixture of the two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino (nitroamino)methyl]amino]-1-oxopentyl]-4-methylpiperidine-2-carboxylate diastereoisomers (6) as olio (ratio 97.7/2.3).

HPLC purity area as the sum of the two diastereoisomers: 98.2%. The product was used partly as it is in the subsequent step.

3Q: Synthesis of (3)

A reactor was filled with 45.2 g of the mixture of the two ethyl (2R,4R)-1-[(2S)-2-[[(1,1-dimethyletoxy)carbonyl] amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino (nitroamino)methyl]amino]-1-oxopentyl]-4-methylpiperidine-2-carboxylate diastereoisomers (6) obtained in 3P and 289 ml of absolute ethanol. The obtained solution was cooled at 15° C. and at this temperature 10.5 g of gaseous HCl were slowly added maintaining the temperature between 15 and 20° C. The solution was triggered using a few mg of (2R,4R)-1-[(2S)-2-amino-5-[[imino(nitroamino)methyl]-amino]-1-oxopentyl]-4-methylpiperidine-2-carboxylate, dihydrochloride hydrochloride ethanol solvate (4) and after 1 hour diluted with 90 ml of ethyl acetate. The reaction mixture was left at 20° C. throughout the night. The suspension was diluted with 270 ml of ethyl acetate and heated at 50° C. After 1.5 hours the mixture was cooled at 20° C. and filtered washing twice with 50 ml of ethyl acetate. Drying at 80° C. 31 g of ethyl (2R,4R)-1-[(2S)-2-amino-5-[[imino(nitroamino)methyl]amino]-1-oxopentyl]-4-methylpiperidine-2-carboxylate dihydrochloride (3) were obtained. The product contains 0.1% of the dihydrochloride ethyl (2S,4S)-1-[(2S)-2-amino-5-[[imino(nitroamino)methyl]amino]-1-oxopentyl]-4-methylpiperidine-2-carboxylate diastereoisomer (11); (the ratio 3/11 is 99.9/0.1).

HPLC purity area as the sum of the two diastereoisomers: 99.6%. The chloride content is 14.0%. Molar yield: 69% starting from a mixture of ethyl (2R,4R)-4-methylpiperidine-2-carboxylate and ethyl (2S,4S)-4-methylpiperidine-2-carboxylate (9/10) with a ratio of 97/3.

3R: Purification of (4)

A reactor is filled with 25 g dihydrochloride (2R,4R)-1-[(2S)-2-amino-5-[[imino(nitroamino)methyl]-amino]-1-oxopentyl]-4-methylpiperidine-2-carboxylate, hydrochloride ethanol solvate (4), (the ratio 4/11 is 98.1/1.9; HPLC purity area as the sum of the two diastereoisomers 4 and 11:

99.2%) 175 ml of absolute ethanol and 175 ml of ethyl acetate. The suspension heating is carried out at 50° C. After 1 hour the mixture is cooled at 20° C. and filtered washing twice with 50 ml of ethyl acetate. Drying at 45° C. 21.4 g of ethyl (2R,4R)-1-[(2S)-2-amino-5-[[imino(nitroamino) methyl]amino]-1-oxopentyl]-4-methylpiperidine-2-carboxylate dihydrochloride ethanol solvate (4) were obtained. The ratio 4/11 is 99.8/0.2. HPLC purity area as the sum of the two diastereoisomers 4 and 11: 99.4%. The chloride content is 14.1%. Yield 86%.

3S: Drying of (4)/Transformation in (3)

The dry (7 g) ethyl (2R,4R)-1-[(2S)-2-amino-5-[[imino(nitroamino)methyl]amino]-1-oxopentyl]-4-methylpiperidine-2-carboxylate dihydrochloride ethanol solvate compound (4) was further dried at a temperature of 80° C. under vacuum for a night obtaining the ethyl (2R,4R)-1-[(2S)-2-amino-5-[[imino(nitroamino)methyl]amino]-1-oxopentyl]-4-methylpiperidine-2-carboxylate dihydrochloride compound (3) (6.5 g). In the NMR spectrum the signal due to ethanol was no longer detectable.

3T: Synthesis of (5) and (6) from Racemic Ester (7) on Pilot Scale 8.2 Kg of CDMT and 77.1 Kg of ethyl acetate are introduced in a reactor. The obtained solution is cooled at 0-5° C. and at this temperature 4.9 Kg of NMM are slowly added obtaining a suspension. After about one hour 14.4 Kg of N-Boc-N'-nitro-L-arginine and 15 Kg of ethyl acetate are added. After about one hour 9.1 Kg of ethyl trans-(±)-4-methylpiperidine-2-carboxylate (7) (70% titre corresponding to 6.4 Kg) in about 45 min are added. After about 2 hours at 0-5° C., the temperature is brought to 20° C. in at least one hour and the reaction mixture is kept under stirring at such temperature throughout the night. The suspension is filtered and the panel washed twice with 12 Kg of ethyl acetate. The organic solution is washed using 52.7 Kg of a 5% aqueous sodium bicarbonate solution, 54.4 Kg of 5% hydrochloric acid and 43 Kg of saturated sodium chloride aqueous solution. The organic phase is concentrated by distillation at reduced pressure obtaining a mixture of two ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) diastereoisomers.

HPLC purity (as the sum of the two diastereoisomers): 97.9%. The product is used as it is in the subsequent step.

3U: Synthesis of ethyl (2R,4R)-1-[(2S)-2-amino-5-[[imino(nitroamino)methyl]amino]-1-oxopentyl]-4-methylpiperidine-2-carboxylate Dihydrochloride Solvated by Ethanol, (4)

To the mixture of ethyl (2R,4R)-1-[(2S)-2-[[(1,1-dimethyletoxy)carbonyl]amino]-5-[[imino(nitroamino)methyl]amino]-1-oxopentyl]-4-methylpiperidine-2-carboxylate (5) and ethyl (2S,4S)-1-[(2S)-2-[[(1,1-dimethyletoxy)carbonyl]amino]-5-[[imino(nitroamino)methyl]amino]-1-oxopentyl]-4-methylpiperidine-2-carboxylate (6) obtained in the previous step (example 3T) 90 kg of absolute ethanol and 97.6 kg of ethyl acetate are added. The obtained solution is cooled at 10-15° C. and at this temperature 4.1 kg of gaseous HCl maintaining the temperature between 10-30° C. are slowly added. The mixture is left at 25° C. throughout the night. The formed suspension is heated at 45-50° C. and at such temperature 30.4 kg of ethyl acetate are added. After about 1.5 hours the mixture is cooled at 20° C. and filtered washing the panel on the filter twice using 16 kg of ethyl acetate. The wet product (2R,4R)-1-[(2S)-2-amino-5-[[imino(nitroamino)methyl]-amino]-1-oxopentyl]-4-methylpiperidine-2-carboxylate, dihydrochloride hydrochloride ethanol solvate (4) has a HPLC area purity as the sum of the two diastereoisomers: 99.7% (the ratio 4/11 is 99.3/0.7).

The solid is used as it is in the subsequent step.

3V: Purification of (4)

A reactor is filled with wet (2R,4R)-1-[(2S)-2-amino-5-[[imino(nitroamino)methyl]-amino]-1-oxopentyl]-4-methylpiperidine-2-carboxylate, dihydrochloride hydrochloride ethanol solvate (4), obtained in the previous step (example 3U), 49 kg of absolute ethanol and 54 kg of ethyl acetate. The suspension heating is carried out at 45-50° C. After 1.5 hours the mixture is cooled at 20° C. and filtered washing twice using 16 Kg of ethyl acetate. Drying at 40-45° C. 7.25 Kg of ethyl (2R,4R)-1-[(2S)-2-amino-5-[[imino(nitroamino)methyl]amino]-1-oxopentyl]-4-methylpiperidine-2-carboxylate dihydrochloride ethanol solvate (4) were obtained. The 4/11 ratio is 99.9/0.1. HPLC area purity as the sum of the two diastereoisomers 4 and 11: 99.7%. The chloride content is 13.8%. The overall yield starting from (7) is of 39%.

Example 4: Resolution, Purification and Unblocking a Base

4A: Resolution; Synthesis of ethyl (2R,4R)-4-methyl-2-piperidinecarboxylate L-tartrate (13)

A reactor was filled with 1,172 ml of acetone and 78 ml of absolute ethanol, 113.7 g of ethyl trans-(±)-4-methylpiperidine-2-carboxylate (7), 88% titre corresponding to 100 g and 89 g of L-tartaric acid. Heating is carried out at 40° C. for 30 minutes and then it is cooled at 20° C. The trigger prepared separately is added, suspending 10 g of ethyl (2R,4R)-4-methyl-2-piperidinecarboxylate L-tartrate (13) in a mixture of acetone (140.6 ml) and absolute ethanol (9.4 ml) and stirring for at least 1 hour, together with 100 ml of acetone/absolute ethanol (15/1). The obtained suspension is filtered after 5 hours at 20° C. and it is washed twice with 100 ml of acetone. 115 g of wet product are obtained. By drying 73 g of product as a mixture of ethyl (2R,4R)-4-methyl-2-piperidinecarboxylate L-tartrate (13) and ethyl (2S,4S)-4-methyl-2-piperidinecarboxylate L-tartrate (14) (ratio 85.9/14.1) diastereoisomer salts are obtained. Molar yield 29%, 13 at 100% from racemic ester 7).

The experiment was repeated maintaining the same experimental conditions but operating at 15° C. instead of 20° C. There was an improvement of the molar yield, which reaches 33-34%, but also an increased impurity of the isolated product, example a 13/14 ratio equal to 70/3.

4B: Purification of (13)

The purity of the product obtained in step 4A can be improved by applying the method of purification described herein.

A reactor was filled with 62 g of a mixture of ethyl (2R,4R)-4-methyl-2-piperidinecarboxylate L-tartrate (13)

and ethyl (2S,4S)-4-methyl-2-piperidinecarboxylate L-tartrate (14) (86/14), diastereomeric salts as obtained in 4A, 800 ml of acetone and 30 ml of absolute ethanol. The obtained suspension was heated at 58° C. and maintained for 30 minutes at such temperature. The suspension was cooled at 35° C. in 1.5 hours and after 1 hour at such temperature filtered washing the panel with 120 ml of acetone. By drying 44 g of ethyl (2R,4R)-4-methyl-2-piperidinecarboxylate L-tartrate (13) were obtained. The product contains 2.7% of the ethyl (2S,4S)-4-methyl-2-piperidinecarboxylate L-tartrate (14) diastereoisomeric salt. Yield 71%.

4C: Unblocking a Base to Obtain an Enriched Ester 65 g of a mixture of ethyl (2R,4R)-4-methyl-2-piperidinecarboxylate L-tartrate (13) and ethyl (2S,4S)-4-methyl-2-piperidinecarboxylate L-tartrate (14) (ratio 86/14), obtained in step 4A, 325 ml of ethyl acetate and 65 ml of water are introduced in a reactor. Cooling is carried out at 15° C. and an aqueous solution (130 ml) of potassium carbonate (31 g) is added in 5 minutes. The obtained biphasic solution is left under stirring at 20° C. for 1 hour, then the phases are separated, the aqueous phase is extracted once again using 130 ml of ethyl acetate, the two organic phases are concentrated by distillation at reduced pressure obtaining 29.4 g of ester (at 100%), with a 99.9% chemical purity. Molar yield 85%. Ethyl (2R,4R)-4-methyl-2-piperidinecarboxylate (9)/ethyl (2S,4S)-4-methyl-2-piperidinecarboxylate (10) (87/13) ratio.

4D: Unblocking a Base to Obtain a Pure Ester (9)

74 g of a mixture of ethyl (2R,4R)-4-methyl-2-piperidinecarboxylate L-tartrate (13) and ethyl (2S,4S)-4-methyl-2-piperidinecarboxylate L-tartrate (14) (ratio 97/3), 370 ml of ethyl acetate and 75 ml of water are introduced in a reactor. Cooling is carried out at 15° C. and an aqueous solution (150 ml) of potassium carbonate (35 g) is added. The obtained biphasic solution is left under stirring at 20° C. for 1 hour, then the phases are separated, the aqueous phase is extracted once again using 150 ml of ethyl acetate, the two organic phases are concentrated by distillation at reduced pressure obtaining 36 g of ester, with a 96.05% potentiometric titre 96.05% then 34.4 g at 100%, with a 99.9% chemical purity. Molar yield: 88%. Ethyl (2R,4R)-4-methyl-2-piperidinecarboxylate (9)/ethyl (2S,4S)-4-methyl-2-piperidinecarboxylate (10) (97.7/2.3) ratio.

What is claimed is:

1. The compound Ethyl (2R,4R)-1-[(2S)-2-amino-5-[[imino(nitroamino)methyl]amino]-1-oxopentyl]-4-methyl-piperidine-2-carboxylate, being a dihydrochloride solvated by ethanol and having a weight/weight chloride content between 11 and 15% and an ethanol content of at least 0.5 mol/mol.

2. The compound of claim 1, having a weight/weight chloride content between 13.5 and 14.5%.

3. The compound of claim 1, having an ethanol content of between 0.7 and 1 mol/mol.

4. The compound of claim 1, having a weight/weight chloride content between 11 and 15% and an ethanol content of between 0.7 and 1 mol/mol.

5. The compound of claim 1, having a weight/weight chloride content between 13.5 and 14.5% and an ethanol content of at least 0.5 mol/mol.

6. The compound of claim 1, having a weight/weight chloride content between 13.5 and 14.5% and an ethanol content of between 0.7 and 1 mol/mol.

* * * * *